US00PP19386P2

(12) United States Plant Patent
Kleinhanns

(10) Patent No.: US PP19,386 P2
(45) Date of Patent: Oct. 28, 2008

(54) ***VERBENA* PLANT NAMED 'VEGAS BRIGHT RED'**

(50) Latin Name: *Verbena hybrida*
Varietal Denomination: Vegas Bright Red

(75) Inventor: Christoph E. Kleinhanns, Gernrode (DE)

(73) Assignee: Hamer Bloemzaden B.V., H.I. Ambacht (NL)

( * ) Notice: Subject to any disclaimer, the term of this patent is extended or adjusted under 35 U.S.C. 154(b) by 0 days.

(21) Appl. No.: 11/827,216

(22) Filed: Jul. 11, 2007

(51) Int. Cl.
*A01H 5/00* (2006.01)

(52) U.S. Cl. ..... Plt./308

(58) Field of Classification Search ..... Plt./308
See application file for complete search history.

*Primary Examiner*—Wendy C. Haas
(74) *Attorney, Agent, or Firm*—Jondle & Associates, P.C.

(57) ABSTRACT

A *Verbena* cultivar particularly distinguished by large, early flowering, bright red flowers, strong branching growth, good garden performance and tolerance to mildew is disclosed.

1 Drawing Sheet

Genus and species: *Verbena hybrida.*
Variety denomination: 'Vegas Bright Red'.

BACKGROUND OF THE NEW PLANT

The present invention comprises a new and distinct cultivar of *verbena,* botanically known as *Verbena hybrida,* and hereinafter referred to by the cultivar name 'Vegas Bright Red'. 'Vegas Bright Red' originated from a hybridization in June 2003 in Quedlinburg, Germany. The female parent was a *verbena* with light red flowers while the male parent was a *verbena* with intense red flowers.

The new cultivar was first propagated in summer of 2006 from mother stock and has been asexually reproduced through vegetative cuttings for four generations. The present invention has been found to retain its distinctive characteristics.

SUMMARY OF THE INVENTION

The following are the most outstanding and distinguishing characteristics of this new cultivar when grown under normal horticultural practices in Quedlinburg, Germany.

1. Large bright red flowers;
2. Early flowering;
3. Strong branching growth;
4. Good garden performance; and
5. Tolerance to mildew.

DESCRIPTION OF THE PHOTOGRAPH

This new *Verbena* plant is illustrated by the accompanying photograph which shows the overall plant habit, including blooms, buds and foliage of the plant in full color, the colors shown being as true as can be reasonably obtained by conventional photographic procedures.

DESCRIPTION OF THE NEW CULTIVAR

The following detailed descriptions set forth the distinctive characteristics of 'Vegas Bright Red'. The data which define these characteristics were collected from asexual reproductions carried out in Quedlinburg, Sachsen-Anhalt, Germany. Data was collected on plants in 12-liter pots in October. Color references are primarily to the R.H.S. Colour Chart of The Royal Horticultural Society of London (R.H.S.) ($4^{th}$ ed).

DETAILED BOTANICAL DESCRIPTION

Classification:
- *Family.*—Verbenaceae.
- *Botanical.*—*Verbena hybrida.*
- *Common name.*—*Verbena.*

Parentage:
- *Female parent.*—*Verbena* plant with light red flowers.
- *Male parent.*—*Verbena* plant with intense red flowers.

Plant:
- *Form.*—Trailing.
- *Growth and branching habit.*—Trailing, basal.
- *Height.*—25.0 cm to 40.0 cm.
- *Width.*—Radius: 30.0 cm to 40.0 cm. Diameter: 60.0 cm to 80.0 cm.
- *Time to produce a finished flowering plant.*—10 to 14 weeks.
- *Time to initiate and develop roots.*—4 to 5 weeks.
- *Root description.*—Fine rooting system, with white to light brown roots.

Stems:
- *Number of branches per plant.*—60 to 90.
- *Length.*—60.0 cm to 100.0 cm.
- *Diameter.*—Radius: 0.1 cm to 0.2 cm. Diameter: 0.2 cm to 0.4 cm.
- *Internode length.*—2.0 cm to 7.0 cm.
- *Color.*—RHS 141A (Green).
- *Anthocyanin.*—Absent.
- *Texture.*—Rough with small hairs.

Leaves:
- *Arrangement.*—Opposite.
- *Immature leaf.*—General color: RHS 141B (Green). Upper surface: RHS 141B (Green). Lower surface: RHS 141C (Lighter green than RHS 141B).

*Mature leaf.*—General color: RHS 137A (Dark green). Upper surface: RHS 141A (Dark green). Lower surface: RHS 141B (Lighter green than RHS 141A). Length: 4.0 cm to 6.0 cm. Width: 1.5 cm to 3.0 cm.

*Shape.*—Oval.

*Apex.*—Differs from round to spiky.

*Base.*—Round running to the short petiole.

*Margin.*—Double ridged.

*Texture.*—Rough, hairy.

*Venation.*—Distinct on the upper surface, very distinct on the lower surface.

*Venation color.*—RHS 141C (Softer green than the leaf).

*Petioles.*—Length: 0.2 cm to 0.7 cm. Diameter: Radius: 0.1 cm to 0.2 cm. Diameter: 0.2 cm to 0.4 cm. Color: RHS 141C (Light green). Texture: Winged from the leaf, some hairs.

Flower buds:

*Shape.*—Nearly covered in haired sepals.

*Length.*—0.5 cm to 1.5 cm.

*Diameter.*—Radius: 0.2 cm to 0.3 cm. Diameter: 0.4 cm to 0.6 cm.

*Color* (*at tight bud*).—RHS 45A (Red).

Inflorescence:

*Blooming habit* (*flowering season*).—May to November.

*Lastingness of individual blooms on the plant.*—About 7 days, but very much dependent on irrigation, fertilizer and temperature.

*Fragrance.*—Soft.

*Inflorescence type.*—Ear type.

*Length of inflorescence.*—2.0 cm to 5.0 cm.

*Diameter of inflorescence.*—Radius: 2.0 cm to 3.5 cm. Diameter: 4.0 cm to 7.0 cm.

*Number of florets per inflorescence.*—20 to 40.

*Peduncle.*—None.

Florets:

*Floret form.*—5 petals, flat flower with long tube.

*Floret length.*—1.5 cm to 3.0 cm.

*Floret diameter.*—Radius: 1.0 cm to 1.5 cm. Diameter: 2.0 cm to 3.0 cm.

*Immature flower.*—General color: RHS 45B (Shiny red). Upper surface: RHS 43A (Shiny red). Lower surface: RHS 43B (Dull red).

*Mature flower.*—General color: RHS 42A (Dark shiny red). Upper surface: RHS 42A (Dark shiny red). Lower surface: RHS 42B (Dull red). Corolla tube length: 2.0 cm to 3.0 cm. Corolla tube color: RHS 141C (Light green).

*Petals.*—Length of lobe: 2.0 cm to 4.0 cm. Diameter of lobe: Radius: 0.3 cm to 0.5 cm. Diameter: 0.6 cm to 1.0 cm. Lobe shape: Soft waved. Apex: Split. Base: Fused. Margin: Soft waved.

Calyx:

*Arrangement.*—Tube shaped.

*Sepals.*—Shape: Fused. Length: 0.5 cm to 1.5 cm. Diameter: Radius: 0.1 cm to 0.2 cm. Diameter: 0.3 cm to 0.4 cm. Color: RHS 142D (Soft light-green). Apex: Spiky. Base: Round. Margin: Fused. Texture: Soft, hairy.

Reproductive organs:

*Stamens.*—Quantity: 5. Shape: with a short stem. Color: RHS 145D (Light yellow-green). Filament length: 0.1 cm to 0.2 cm. Filament diameter: Radius: Less than 0.1 cm. Diameter: Less than 0.1 cm.

*Anther.*—Shape: Oval. Color: RHS 145D (Light yellow-green). Length: 0.1 cm to 0.2 cm. Diameter: Radius: Less than 0.1 cm. Diameter: 0.1 cm.

*Pollen.*—Color: RHS 145D (Light yellow-green). Amount: Moderate.

*Pistils.*—Number: 1. Length: 1.5 cm to 2.0 cm. Diameter: Radius: Less than 0.1 cm. Diameter: Less than 0.1 cm. Stigma: Color: RHS 141B (Green). Shape: Round to oval. Length: 0.1 cm. Diameter: Radius: Less than 0.1 cm. Diameter: Less than 0.1 cm. Style: Color: RHS 141B (Green). Length: 1.4 cm to 1.9 cm. Diameter: Radius: Less than 0.1 cm. Diameter: Less than 0.1 cm. Shape: Running wider as getting nearer to the stigma.

Seeds:

*Color.*—RHS 152A (Greenish brown).

*Length.*—0.3 cm to 0.8 cm.

*Diameter.*—Radius: Less than 0.1 cm to 0.1 cm. Diameter: Less than 0.1 cm to 0.2 cm. Shape: Rough.

Disease and insect resistance: Tolerant to powdery mildew.

COMPARISON WITH KNOWN CULTIVARS

'Vegas Bright Red' differs from the female parent *Verbena* plant in that the female parent has a more trailing growth habit than 'Vegas Bright Red'. Additionally, the female parent of 'Vegas Bright Red' has a light red flower color while 'Vegas Bright Red' has a red flower color.

'Vegas Bright Red' differs from the male parent *Verbena* plant in that the male parent does not have a trailing growth habit while 'Vegas Bright Red' does have a trailing growth habit. Additionally, the male parent has a more intense red flower color than 'Vegas Bright Red'.

'Vegas Bright Red' differs from the commercial *Verbena* variety 'Star Dream Patio Red' (unpatented) in that 'Vegas Bright Red' has a red flower color that does not fade, while 'Star Dream Patio Red' has a red flower color that fades with time. Additionally, 'Star Dream Patio Red' has less of a trailing growth habit than 'Vegas Bright Red'.

I claim:

1. A new and distinct cultivar of *Verbena* plant as described and shown herein.

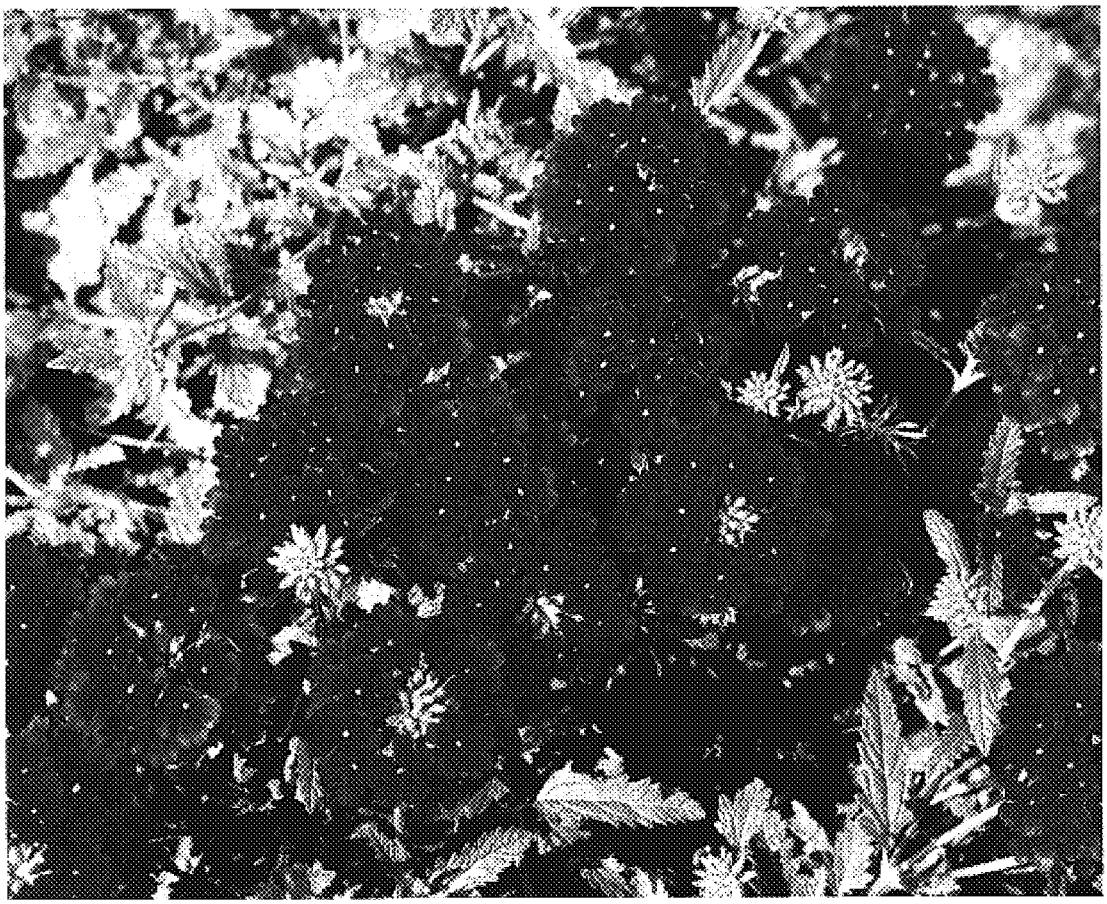

* * * * *